(12) United States Patent
Hayden

(10) Patent No.: US 9,468,404 B2
(45) Date of Patent: Oct. 18, 2016

(54) BLOOD SAMPLING TUBE WITH INTEGRATED SENSOR DEVICE

(71) Applicant: Oliver Hayden, Herzogenaurach (DE)

(72) Inventor: Oliver Hayden, Herzogenaurach (DE)

(73) Assignee: Siemens Aktiengesellschaft, München (DE)

( * ) Notice: Subject to any disclaimer, the term of this patent is extended or adjusted under 35 U.S.C. 154(b) by 13 days.

(21) Appl. No.: 14/378,143

(22) PCT Filed: Jan. 22, 2013

(86) PCT No.: PCT/EP2013/051107
§ 371 (c)(1),
(2) Date: Aug. 12, 2014

(87) PCT Pub. No.: WO2013/120665
PCT Pub. Date: Aug. 22, 2013

(65) Prior Publication Data
US 2015/0011847 A1  Jan. 8, 2015

(30) Foreign Application Priority Data
Feb. 14, 2012 (DE) .................. 10 2012 202 197

(51) Int. Cl.
*A61B 5/157* (2006.01)
*A61B 5/154* (2006.01)
(Continued)

(52) U.S. Cl.
CPC ............... *A61B 5/157* (2013.01); *A61B 5/145* (2013.01); *A61B 5/15003* (2013.01); *A61B 5/153* (2013.01); *A61B 5/154* (2013.01); *A61B 5/15087* (2013.01); *A61B 5/150221* (2013.01); *A61B 5/150251* (2013.01); *A61B 5/150389* (2013.01); *A61B 5/150503* (2013.01); *A61B 5/150732* (2013.01); *A61B 5/150755* (2013.01); *A61B 5/150854* (2013.01);
(Continued)

(58) Field of Classification Search
CPC ................ A61B 5/150099; A61B 5/150251; A61B 5/154; A61B 5/157; A61B 5/15003; A61B 5/153
See application file for complete search history.

(56) References Cited

U.S. PATENT DOCUMENTS 4,339,317 A   7/1982  Meiattini et al.
4,558,589 A * 12/1985  Hemmes ..................... 73/64.42
(Continued)

FOREIGN PATENT DOCUMENTS

CN  1713849 A  12/2005
CN  102378595 A  3/2012
(Continued)

OTHER PUBLICATIONS

German Office Action dated May 31, 2012 for corresponding German Patent Application No. 10 2012 202 197.3, with English translation.
(Continued)

*Primary Examiner* — Paul Hyun
(74) *Attorney, Agent, or Firm* — Lempia Summerfield Katz LLC

(57) ABSTRACT

A blood-sampling tube with a first fluid-receiving chamber for receiving a fluid is described, where the first fluid-receiving chamber may be connected to at least one fluid channel that has a sensor device for measuring at least one biochemical function of the fluid passed through the fluid channel, where the measured biochemical function of the fluid may be read out from the sensor device via a data interface of the blood-sampling tube.

18 Claims, 1 Drawing Sheet

(51) Int. Cl.
  *A61B 5/15*      (2006.01)
  *A61B 5/153*     (2006.01)
  *A61B 5/145*     (2006.01)
  *A61B 5/05*      (2006.01)
  *A61B 5/1455*    (2006.01)

(52) U.S. Cl.
  CPC .. *A61B 5/150862* (2013.01); *A61B 5/150923* (2013.01); *A61B 5/05* (2013.01); *A61B 5/1455* (2013.01); *A61B 5/150099* (2013.01); *A61B 5/150946* (2013.01)

(56) References Cited

U.S. PATENT DOCUMENTS

| | | |
|---|---|---|
| 5,025,798 A | 6/1991 | Schindele |
| 5,029,583 A | 7/1991 | Meserol et al. |
| 5,046,496 A * | 9/1991 | Betts et al. ............. 600/352 |
| 5,048,539 A | 9/1991 | Schindele |
| 5,700,695 A * | 12/1997 | Yassinzadeh et al. ........ 436/180 |
| 6,572,564 B2 | 6/2003 | Ito et al. |
| 2003/0065536 A1 | 4/2003 | Hansen et al. |
| 2008/0177154 A1 | 7/2008 | Hansen et al. |
| 2009/0018426 A1 * | 1/2009 | Markle et al. ............. 600/365 |
| 2011/0009812 A1 | 1/2011 | Brown |
| 2012/0022354 A1 | 1/2012 | Beyer et al. |
| 2012/0165698 A1 | 6/2012 | Kuhr et al. |

FOREIGN PATENT DOCUMENTS

| | | |
|---|---|---|
| DE | 1038310 B | 9/1958 |
| DE | 2543576 A1 | 4/1977 |
| DE | 2927048 A1 | 2/1980 |
| DE | 4333615 A1 | 4/1995 |
| DE | 60126448 T2 | 6/2007 |
| EP | 0706825 | 4/1996 |
| EP | 2236077 | 10/2010 |
| EP | 2281507 A1 | 2/2011 |

OTHER PUBLICATIONS

PCT Internation Search Report and Written Opinion cited in PCT/EP2013/051107, mailed May 7, 2013.

Chinese Office action for related Chinese Application No. 201380009378.1, dated Sep. 6, 2015, with English Translation.

* cited by examiner

BLOOD SAMPLING TUBE WITH INTEGRATED SENSOR DEVICE

CROSS-REFERENCE TO RELATED APPLICATIONS

The present patent document is a §371 nationalization of PCT Application Serial Number PCT/EP2013/051107, filed Jan. 22, 2013, designating the United States, which is hereby incorporated by reference, and this patent document also claims the benefit of DE 10 2012 202 197.3, filed on Feb. 14, 2012, which is also hereby incorporated by reference.

TECHNICAL FIELD

The embodiments relate to a blood sampling tube with an integrated sensor device for measuring a biochemical function of a fluid, in particular, a fluid withdrawn from an organism.

BACKGROUND

Blood sampling tubes are widespread and conventionally serve as a sample transporting container, in particular, for taking and preparing blood samples. Blood sampling tubes enable transportation of the withdrawn blood and short-term storage of the withdrawn samples. Similar systems also exist for other bodily fluids, in particular, for urine samples.

Conventionally, there are two different systems that withdraw samples, either by aspiration or by negative pressure. There are tubes with different add-ons in both systems. The design of a blood sampling tube with an aspiration system approximates that of a syringe. By pulling out a plunger, negative pressure that accelerates taking of the fluid is created. By contrast, negative pressure already exists in advance in a blood sampling tube in the case of a blood sampling tube in a negative pressure system. If the blood sampling tube is placed onto an adapter connected to a puncturing cannula, the fluid, in particular blood, is suctioned by the negative pressure present. In both systems, the withdrawn blood may be stabilized for storage or transportation purposes for example by citrate.

In the case of conventional systems, it is necessary to withdraw the withdrawn fluid, (e.g., the withdrawn blood), from the blood sampling tube for further analysis, for example, by pipetting. This procedure has a number of disadvantages. First of all, withdrawing the fluid with the aid of a pipetting device requires a certain amount of manual dexterity on the part of the person taking the sample such that only appropriately educated staff comes into question for this procedure. Furthermore, such a pipetting device for withdrawing the fluid from the blood sampling tube must also be available in situ. This provides that the person wishing to withdraw the blood for analysis purposes has an appropriate pipetting device in situ. However, an in situ device may not always be provided, for example, in a domicile of a patient. Furthermore, withdrawing the fluid from the blood sampling tube is relatively difficult and consumes much time, as a result of which the analysis of the biochemical functions of the withdrawn fluid is delayed.

SUMMARY AND DESCRIPTION

It is therefore an object of the present embodiments to develop a blood sampling tube that enables fast and reliable acquisition of a biochemical function of a fluid and which, simultaneously, is easy to handle.

The scope of the present invention is defined solely by the appended claims and is not affected to any degree by the statements within this summary. The present embodiments may obviate one or more of the drawbacks or limitations in the related art.

The embodiments provide a blood sampling tube including a first fluid chamber for receiving a fluid. The first fluid receiving chamber may be connected to at least one fluid channel including a sensor device for measuring at least one biochemical function of the fluid passed through the fluid channel. The measured biochemical function of the fluid may be read out from the sensor device via a data interface of the blood sampling tube.

In one possible embodiment of the blood sampling tube, the fluid passed through the fluid channel reaches a second fluid receiving chamber to which negative pressure may be applied.

In an alternative embodiment, negative pressure may be applied directly to the fluid channel.

In one possible embodiment of the blood sampling tube, the two fluid receiving chambers are separated in each case from the fluid channel by a rupture disk or by a valve.

In one possible embodiment of the blood sampling tube, a needle may be placed onto the blood sampling tube, by which needle a bodily fluid, in particular venous blood or urine, may be withdrawn from an organism.

In one possible embodiment of the blood sampling tube, an incubation device for adding reagents to the fluid passed through the fluid channel is provided in the fluid channel.

In a further possible embodiment of the blood sampling tube, the fluid channel lying between the incubation device and the sensor device has a predetermined fluid channel volume, where this fluid channel volume and a flow velocity of the fluid flowing through the fluid channel determine an adjustable reaction time of the reagents, dispensed by the incubation device, with the fluid.

In a further possible embodiment of the blood sampling tube, the flow velocity of the fluid through the fluid channel depends upon an adjustable pressure drop between the two fluid receiving chambers of the blood sampling tube.

In one possible embodiment of the blood sampling tube, the sensor device measures the biochemical function of the fluid contactlessly.

In one possible embodiment of the blood sampling tube, the sensor device includes at least one magnetoelastic capillary tube through which the fluid to be examined is passed.

In one possible embodiment of the blood sampling tube, a resonant frequency of the magnetoelastic capillary tube, which depends on a surface load on the inner wall of the magnetoelastic capillary tube, may be read out contactlessly for determining the biochemical function of the fluid.

In a further embodiment of the blood sampling tube, the sensor device establishes the biochemical function of the fluid by an optical transmission or stray light measurement.

In a further possible embodiment of the blood sampling tube, the data interface of the blood sampling tube is a wireless data interface.

In a further possible embodiment of the blood sampling tube, the data interface of the blood sampling tube is a wired data interface.

In a further possible embodiment of the blood sampling tube, the data interface of the blood sampling tube has a removable data memory card.

In one possible embodiment of the blood sampling tube, the data interface of the blood sampling tube transmits the measured biochemical function of the fluid to an external readout instrument.

In one possible embodiment of the blood sampling tube, the external readout instrument connected to the data interface of the blood sampling tube is a mobile hand-held device, in particular a mobile communications device.

In one possible embodiment of the blood sampling tube, the blood sampling tube is a disposable product.

DETAILED DESCRIPTION

Figure 1:
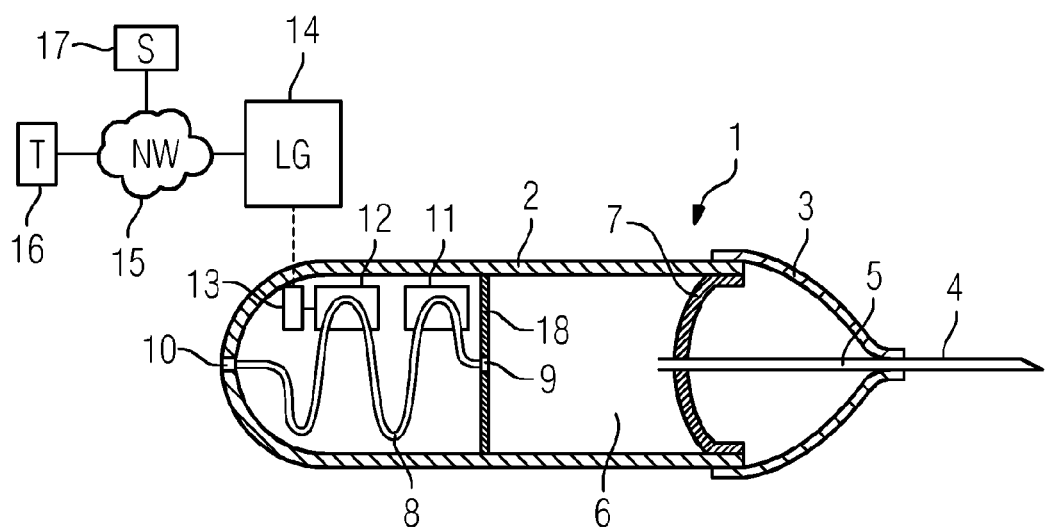
FIG. 1 depicts a first exemplary embodiment for a blood sampling tube.

It is possible to identify in FIG. 1 that a blood sampling tube 1 includes a housing 2 that, for example, may include a transparent plastic material. A cap 3 that carries a needle 4 for withdrawing a fluid F may be placed onto the housing 2. The needle 4 is suitable for withdrawing a fluid F from an organism, where the fluid F may be, e.g., venous blood or urine. The withdrawn fluid F reaches into a first fluid receiving chamber 6 of the blood sampling tube 1 via a cannula 5.

By way of example, in the process, the cannula 5 penetrates an elastic rubber 7 that seals the housing 2 of the blood sampling tube 1. The first fluid receiving chamber 6 serves for receiving the withdrawn fluid F, where the first fluid receiving chamber 6 may be connected to at least one fluid channel 8, for example, through a rupture disk 9. The fluid receiving chamber or the compartment 6 is therefore separated from the fluid channel 8 by a rupture disk or sealing disk 9, where the sealing disk or the rupture disk may be opened or ruptured by applying a high negative pressure.

In an alternative embodiment, it is also possible to use a controllable valve in place of the rupture disk or sealing disk 9. In one possible embodiment, this valve is a micromechanical valve that may be controlled for opening and closing.

In the embodiment depicted in FIG. 1, the fluid channel 8 has a meandering embodiment, where the fluid channel is separated at a distal end from the first fluid receiving chamber 6 by the rupture disk 9. At the other end of the meandering fluid channel 8, provisions may be made for a further rupture disk or sealing disk 10 that seals the housing 2 of the blood sampling tube from the outside. This rupture disk or sealing disk 10 may likewise be opened by applying negative pressure, e.g., suction pressure.

In the exemplary embodiment depicted in FIG. 1, the fluid situated in the fluid receiving chamber 6 is passed through the fluid channel 8 after rupturing or opening the sealing disks or rupture disks 9, 10, where the fluid F first of all reaches an incubation device 11. The incubation device 11 is designed to add reagents, (e.g., biochemical substances), to the fluid F passing through the fluid channel 8. These reagents emitted by the incubation device 11 may perform a biochemical reaction with the fluid F passing therethrough. After the reagents were added to the passing-through fluid F by the incubation device 11, the fluid F reaches a sensor device 12 after a certain path. The sensor device measures at least one biochemical function of the fluid F passing through the fluid channel 8. By way of example, the sensor device 12 may be situated on a micro-fluid chip. The fluid F passing therethrough may be, for example, withdrawn venous blood, where the sensor device 12 measures a biochemical function of the blood, (e.g., the coagulation properties thereof).

Furthermore, a thrombocyte function of the withdrawn venous blood may be measured by the sensor device 12. The biochemical function of the fluid F, measured by the sensor device 12, may be read out via a data interface 13 of the blood sampling tube 1. The data interface 13 is directly connected to the sensor device 12, as depicted in FIG. 1.

In the embodiment depicted in FIG. 1, the data interface 12 is a wireless data interface, where the data may be read out wirelessly from the data interface 13 by an external readout instrument 14. Alternatively, the data interface 13 may also be a wired data interface, where data may be read out by the readout instrument 14, depicted in FIG. 1, via a cable. In a further possible embodiment, the data interface 13 is formed by a removable data memory card, which may be removed from the blood sampling tube 1. In the exemplary embodiment depicted in FIG. 1, the readout instrument 14 is connected via a data network 15, e.g., the Internet, to a terminal 16 and a server 17 that, for example, has access to a medical database. In this manner, it is possible to directly transmit the data in respect of the biochemical function of the fluid F, established by the sensor unit 12, to the readout instrument 14 and the data network 15 to a distant terminal 16.

By way of example, the blood withdrawn from the patient by a paramedic, (e.g., in a domicile of a patient), may be analyzed in respect of a biochemical function by the sensor device 12. The analysis result may be transmitted via the network to a distant terminal 16, in front of which a medically qualified person, (e.g., a laboratory medical practitioner), is seated. Furthermore, the transmitted data may be directly stored for further examination in a database of the server 17 depicted in FIG. 1.

As depicted in FIG. 1, the fluid channel 8 has a predetermined path between the incubation device 11 and the sensor device 12, and therefore forms a predetermined fluid channel volume. This fluid channel volume and a flow velocity of the fluid F passing through the fluid channel 8 determine an adjustable reaction time of the reagents emitted by the incubation device 11 with the fluid withdrawn from the organism. The flow velocity of the fluid is determined in this case by an adjustable pressure gradient (AP) in the fluid channel 8. In this manner, a sufficiently long reaction time T with the added reagents may be achieved.

In one embodiment, the biochemical function of the fluid F is measured contactlessly with the aid of the sensor device 12. In one possible embodiment, the sensor device 12 includes at least one magnetoelastic capillary tube, through which the fluid F to be examined is passed. In one possible embodiment, a resonant frequency fR of the magnetoelastic capillary tube may be measured and read out in the process. This resonant frequency fR depends on a surface load on the inner wall of the magnetoelastic capillary tube of the sensor device 12, where a biochemical function of the fluid, (e.g., a thrombocyte function of blood), may be established contactlessly with the aid of the acquired resonant frequency fR. In an alternative embodiment, the biochemical function of the fluid is established by the sensor device 12 by an optical transmission or stray light measurement.

The blood sampling tube 1 depicted in FIG. 1 may be embodied as a disposable product. For example, the blood sampling tube 1 is not reused after establishing the biochemical function. The negative pressure that, for example, causes the rupture disks 9, 10 depicted in FIG. 1 to rupture, may be generated in different ways. By way of example, negative pressure may be applied to the rupture disk 10 from the outside that initially causes the rupture disk 10 to rupture and subsequently causes the rupture disk 9 to rupture, and so the fluid F situated in the fluid receiving chamber 6 passes through the fluid tube 8 to the ruptured disk 10.

In the embodiment depicted in FIG. 1, the blood sampling tube includes a fluid channel 8. In an alternative embodiment, it is also possible for a plurality of fluid channels 8 to be provided in parallel, where each fluid channel 8 includes an incubation device 11 and a sensor device 12. The fluid F emerging through the ruptured disk 10 may be received by a further fluid receiving chamber or a waste compartment.

Figure 2:
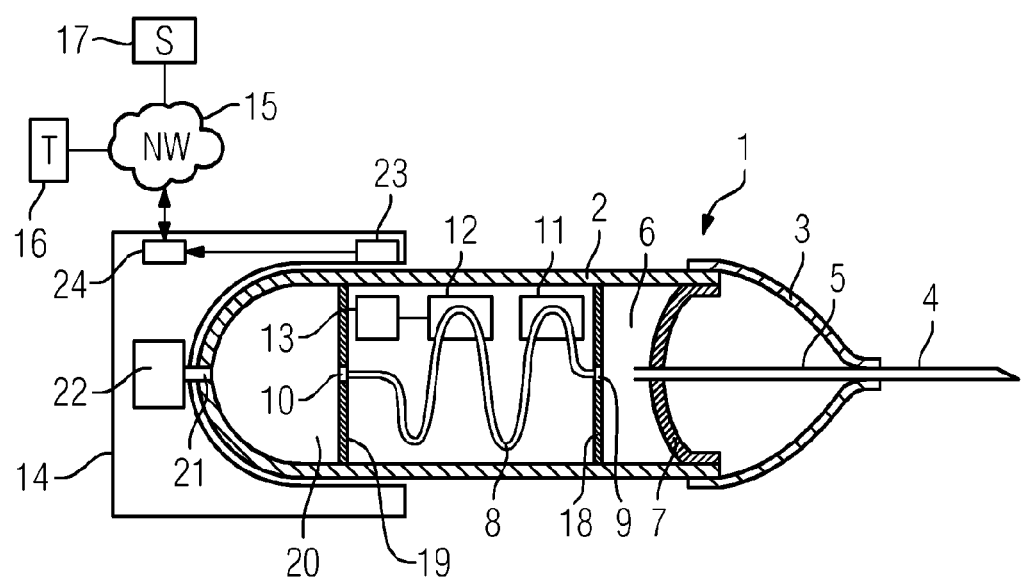
FIG. 2 depicts a second exemplary embodiment for a blood sampling tube.

FIG. 2 depicts an exemplary embodiment in which the blood sampling tube 1 includes an integrated second fluid receiving chamber or a waste compartment 20. It is possible to identify from FIGS. 1 and 2, that rupture disks 9, 10 provided in the depicted exemplary embodiment are arranged in separating walls 18, 19. After rupturing the rupture disk 10, the fluid F situated in the first fluid chamber 6 flows through the fluid channel 8 into the second fluid receiving chamber 20, which likewise is situated in the housing 2 of the blood sampling tube 1.

By an opening 21, which is situated in the housing 2 of the blood sampling tube 1, the second fluid receiving chamber 20 or the waste compartment may be connected to a negative pressure device 22 of an external instrument in order to build up negative pressure in the waste compartment 20 that, in turn, brings the two rupture disks 9, 10 to rupture such that the fluid F flows from the first fluid receiving chamber 6 into the second fluid receiving chamber 20 via the fluid channel 8. The fluid F flowing therethrough is analyzed by the sensor device 12 for establishing a biochemical function of the fluid. What the provision of the second fluid receiving chamber 20 achieves is that the blood sampling tube 1 forms a closed system, and so the examining person does not come into contact with the withdrawn fluid F, (e.g., blood). This is advantageous since the withdrawn fluid F, (e.g., blood), may potentially be infectious.

In the embodiment depicted in FIG. 2, the negative pressure device 22 is also integrated into the readout instrument 14, where the readout instrument 14 includes an integrated data interface 23 that, in a wired or wireless manner, reads out data from the data interface 13 of the blood sampling tube 1. In the embodiment depicted in FIG. 2, the read-out data is directly transmitted to the distant terminal 16 and/or the distant server 17 via a further data interface 24 of the readout instrument 14 and via the network 15.

In the exemplary embodiment depicted in FIG. 2, the blood sampling tube 1 may be inserted into the readout instrument 14, where the readout instrument 14 additionally provides that appropriate negative pressure is applied to the inserted blood sampling tube 1. After withdrawing and analyzing the fluid F, the blood sampling tube 1 may additionally be stored. This is useful, particularly if a peculiarity emerges in the analysis of the biochemical function of the fluid F, which may be verified by a second measurement. In a possible embodiment, a stabilizing substance, (e.g. citrate), may be prefilled in the blood sampling tube 1 for storing the withdrawn fluid F.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A blood sampling tube comprising:
a first fluid receiving chamber for receiving a fluid, wherein the first fluid receiving chamber is connected to at least one fluid channel comprising a sensor device for measuring at least one biochemical function of the fluid passed through the at least one fluid channel,
wherein the at least one measured biochemical function of the fluid is configured to be read out from the sensor device via a data interface of the blood sampling tube,
wherein the sensor device is configured to measure the at least one biochemical function of the fluid contactlessly, and
wherein the sensor device comprises at least one magnetoelastic capillary tube through which the fluid to be examined is passed.

2. The blood sampling tube as claimed in claim 1 futher comprising a second fluid receiving chamber, wherein the fluid is passed through the fluid channel to the second fluid receiving chamber by negative pressure.

3. The blood sampling tube as claimed in claim 2, wherein the first fluid receiving chamber and the second fluid receiving chamber are separated from the at least one fluid channel by rupture disks or by valves.

4. The blood sampling tube as claimed claim 2, wherein an incubation device for adding reagents to the fluid passed through the at least one fluid channel is provided in the at least one fluid channel.

5. The blood sampling tube as claimed in claim 4, wherein the at least one fluid channel has a predetermined fluid channel volume between the incubation device and the sensor device, wherein the predetermined fluid channel volume and a flow velocity of the fluid passed through the at least one fluid channel determine an adjustable reaction time of the reagents, dispensed by the incubation device, with the fluid.

6. The blood sampling tube as claimed in claim 5, wherein the flow velocity of the fluid passed through the at least one fluid channel depends upon an adjustable pressure drop between the first fluid receiving chamber and the second fluid receiving chamber of the blood sampling tube.

7. The blood sampling tube as claimed in claim 1, further comprising a needle placed onto the blood sampling tube and configured to withdraw a bodily fluid from an organism.

8. The blood sampling tube as claimed in claim 7, wherein the bodily fluid is venous blood or urine.

9. The blood sampling tube as claimed claim 1, wherein an incubation device is provided in the at least one fluid channel for adding reagents to the fluid passed through the fluid channel.

10. The blood sampling tube as claimed in claim 9, wherein the at least one fluid channel has a predetermined fluid channel volume between the incubation device and the sensor device, wherein the predetermined fluid channel volume and a flow velocity of the fluid passed through the at least one fluid channel determine an adjustable reaction time of the reagents, dispensed by the incubation device, with the fluid.

11. The blood sampling tube as claimed in claim 10, wherein the flow velocity of the fluid passed through the at least one fluid channel depends upon an adjustable pressure drop between the first fluid receiving chamber and a second fluid receiving chamber of the blood sampling tube. depends on a surface load on an inner wall of the at least one magnetoelastic capillary tube, is configured to be read out contactlessly for determining the at least one biochemical function of the fluid.

12. The blood sampling tube as claimed in claim 1, wherein a resonant frequency of the at least one magnetoelastic capillary tube, which depends on a surface load on an inner wall of the at least one magnetoelastic capillary tube, is configured to be read out contactlessly for determining the at least one biochemical function of the fluid.

13. The blood sampling tube as claimed in claim 1, wherein the sensor device establishes the at least one biochemical function of the fluid by an optical transmission or stray light measurement.

14. The blood sampling tube as claimed in claim 1, wherein the data interface of the blood sampling tube comprises a wireless or wired data interface or a removable data memory card, wherein the card is removable from the blood sampling tube.

15. The blood sampling tube as claimed in claim 1, wherein the data interface of the blood sampling tube transmits the at least one measured biochemical function of the fluid to an external readout instrument.

16. The blood sampling tube as claimed in claim 15, wherein the external readout instrument connected to the data interface is a mobile hand-held device.

17. The blood sampling tube as claimed in claim 16, wherein the mobile hand-held device is a mobile communications device.

18. The blood sampling tube as claimed in claim 1, wherein the blood sampling tube is a disposable product.

* * * * *